(12) United States Patent
Salama

(10) Patent No.: US 6,527,755 B1
(45) Date of Patent: Mar. 4, 2003

(54) FECES CONTROL DEVICE

(76) Inventor: Fouad A. Salama, P.O. Box 1568, 45210 El Prado Rd., Temecula, CA (US) 92593

(*) Notice: Subject to any disclaimer, the term of this patent is extended or adjusted under 35 U.S.C. 154(b) by 158 days.

(21) Appl. No.: 09/839,011

(22) Filed: Apr. 20, 2001

(51) Int. Cl.⁷ .................................................. A61F 5/44
(52) U.S. Cl. ................. 604/348; 604/328; 604/327; 604/332; 604/326; 604/337; 604/338; 604/339; 604/341; 604/352
(58) Field of Search ................................ 604/328, 326, 604/327, 332, 337, 338, 339, 341, 348, 352

(56) References Cited

U.S. PATENT DOCUMENTS

| | | | | |
|---|---|---|---|---|
| 2,149,053 A | * | 2/1939 | Hollister | 604/328 |
| 4,067,335 A | * | 1/1978 | Silvanov | 604/328 |
| 4,217,664 A | | 8/1980 | Faso | |
| 4,261,340 A | | 4/1981 | Baumel et al. | |
| 4,338,937 A | | 7/1982 | Lerman | |
| 4,596,554 A | * | 6/1986 | Dastgeer | 604/540 |
| 4,619,648 A | * | 10/1986 | Rath et al. | 604/326 |
| 4,781,176 A | | 11/1988 | Ravo | |
| 4,941,869 A | | 7/1990 | D'Amico | |
| 4,968,294 A | * | 11/1990 | Salama | 600/30 |
| 5,306,226 A | * | 4/1994 | Salama | 600/29 |
| 5,509,889 A | | 4/1996 | Kalb et al. | |
| 5,513,659 A | | 5/1996 | Buuck et al. | |
| 5,634,877 A | * | 6/1997 | Salama | 600/29 |
| 5,741,239 A | * | 4/1998 | Mulholland | 604/328 |
| 5,766,249 A | | 6/1998 | Griffith | |
| 5,795,288 A | | 8/1998 | Choen et al. | |
| 5,893,826 A | * | 4/1999 | Salama | 600/31 |
| 5,941,860 A | * | 8/1999 | Wheeler | 604/327 |

* cited by examiner

Primary Examiner—John J. Calvert
Assistant Examiner—Angela J Grayson
(74) Attorney, Agent, or Firm—McKee, Voorhees & Sease, P.L.C.

(57) ABSTRACT

A feces control device includes a tubular member in which an inflatable balloon is positioned on one interior sidewall for closing the passageway to movement of feces when the balloon is expanded and allowing flow when the balloon is contracted against the sidewall to which it is attached. A second balloon on the inner end of the tubular member when inflated presses against the inner end of an umbrella mounted on the inner end of the tubular member thereby expanding the umbrella to a radially outwardly and forwardly extending sealing position in the stoma or rectum. When the umbrella balloon is deflated, the umbrella memory causes it to collapse to a position coaxial with the tubular member. Inflation passageways in the sidewall of the tubular member may include tube portions for inflating the balloons or removing the device from the rectum.

42 Claims, 5 Drawing Sheets

FECES CONTROL DEVICE

BACKGROUND OF THE INVENTION

Persons requiring ostomy procedures or being fecally incontinent have need for a feces control device that will not leak and is simple to install, operate and remove.

BRIEF SUMMARY OF THE INVENTION

The feces control devices of this invention meet the needs of persons having had an ostomy procedure or are fecally incontinent. The control devices of this invention can be positioned either in a stoma or the anus.

Two inflatable balloons are provided, the first being a spherical shaped balloon positioned on the inside wall of a tubular member for being inflated to close off the passageway through the tubular member or being deflated to allow voiding with the balloon withdrawing against the passageway sidewall to which it is attached. The second balloon being doughnut-shaped is positioned around the inner end of the tubular member and against an umbrella radiating outwardly and forwardly when in an expanded condition. The umbrella balloon when inflated presses against the umbrella moving it to its open position and when deflated the memory of the umbrella causes it to collapse to a coaxial position with the tubular member allowing withdrawal of the control device from the stoma or rectum.

An adapter end piece is attached to the outer end of the tubular member for connecting the tubular member to a detachable bag for collection of waste material. A pair of conduit pieces on the bag adapter end piece are received telescopically in conduits in the sidewall of the tubular member extending to the balloon valve and the umbrella balloon. Outer free ends of the conduit portions in the adapter end piece include self sealing micro valves which are engagable by an inflation device such as a hypodermic needle or a cannula for inflating and deflating the balloons.

In a second embodiment, the outer end of the tubular member may include inflation tubes connected to the conduits in the tubular member sidewall such that an inflation device can be connected to the tubes for inflating and deflating the balloon valve and the umbrella valve. The inflation tubes can also be used for pulling on to remove the control device from the rectum.

DETAILED DESCRIPTION OF THE PREFERRED EMBODIMENT

Figure 1:
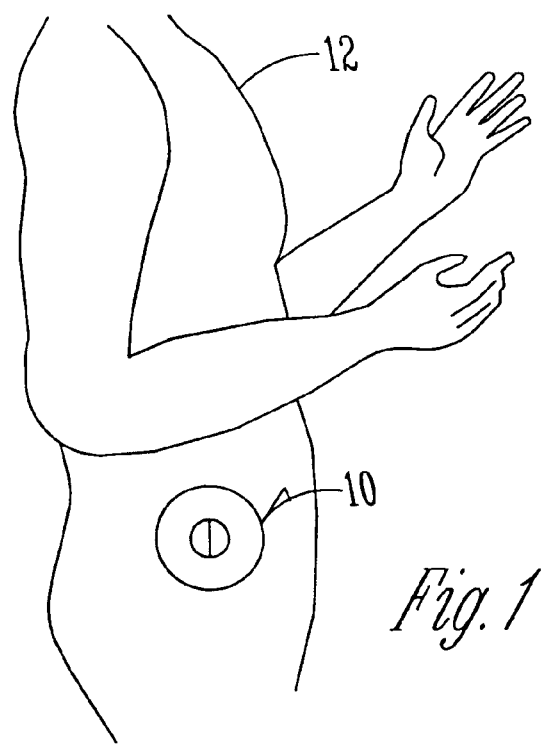
FIG. 1 is a fragmentary side view of the control device of this invention being positioned in a stoma of a person.
Figure 2:
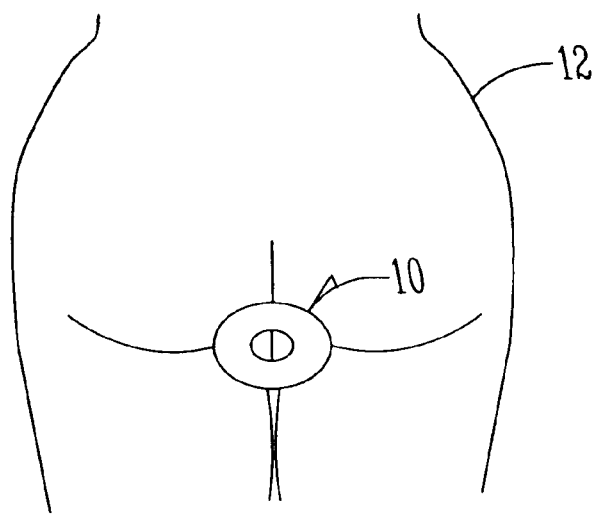
FIG. 2 is a view similar to FIG. 1 but showing the control device positioned in a person's rectum.

The feces control device of this invention is referred to generally in FIG. 1 by the Reference Numeral 10 and is shown positioned in a stoma on the side of a person 12. In FIG. 2, the control device 10 is positioned in the rectum of the person 12.

Figure 3:
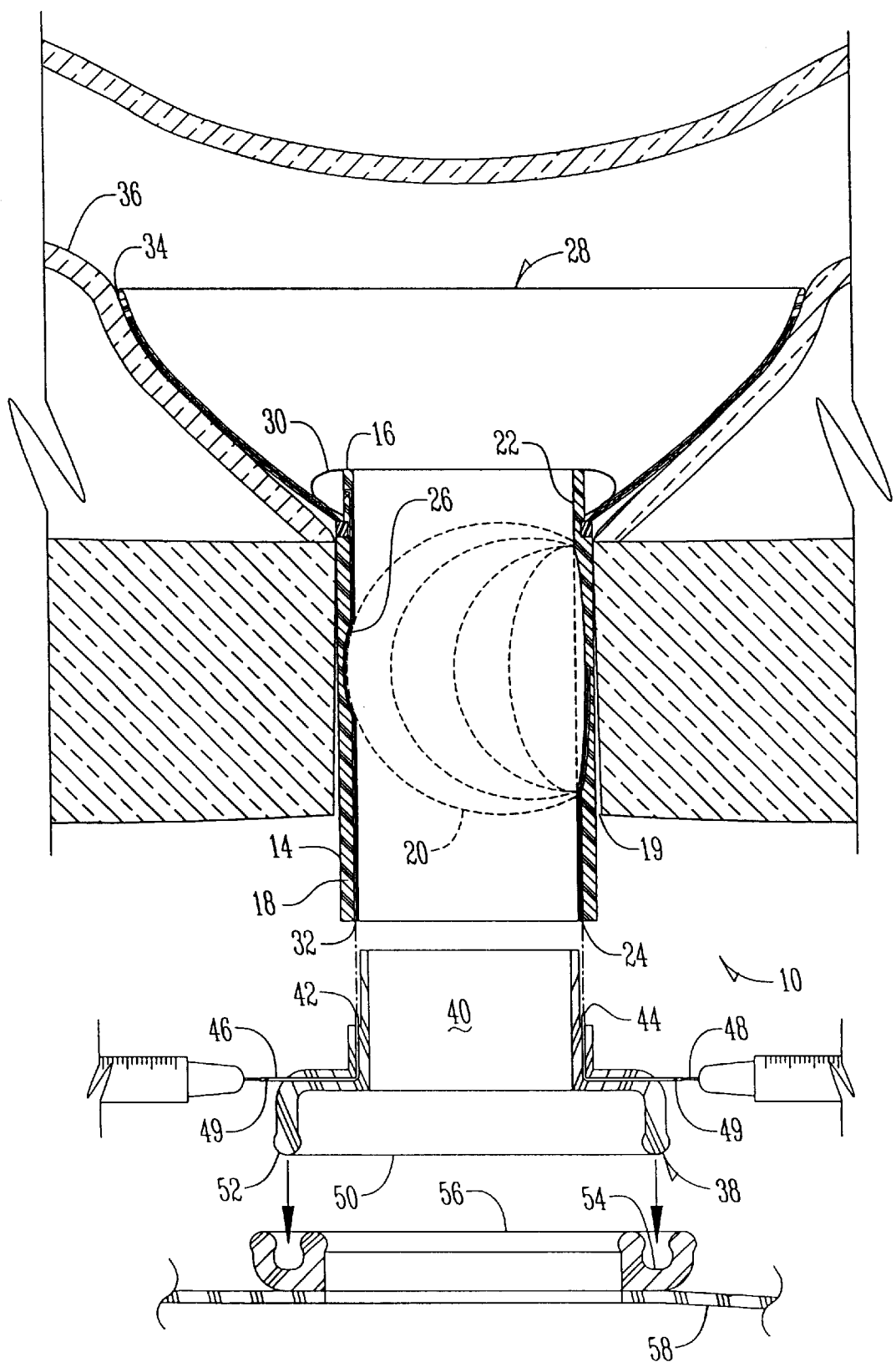
FIG. 3 is a cross-sectional view of the control device positioned in a stoma.
Figure 4:
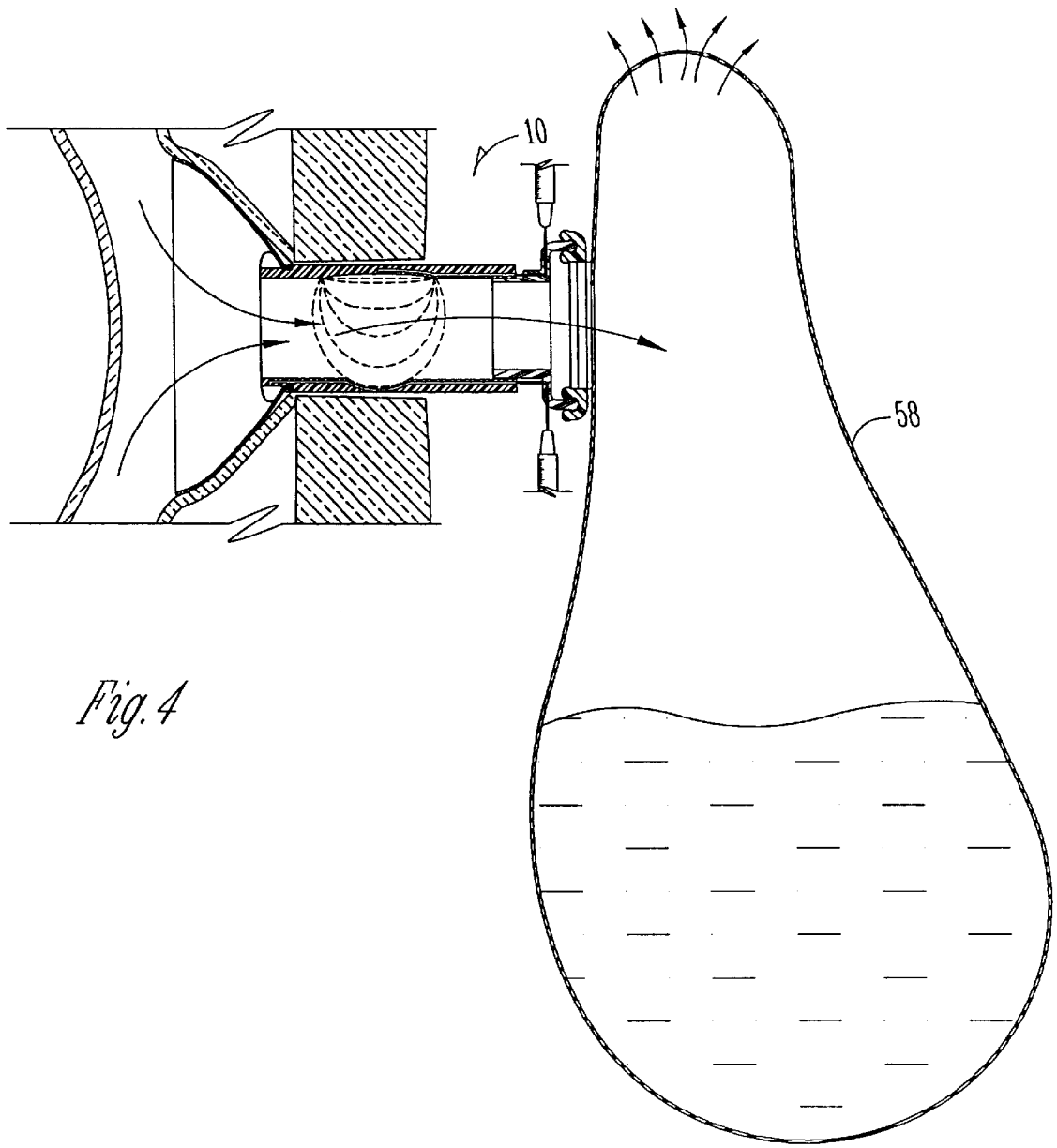
FIG. 4 is a view similar to FIG. 3 but showing the bag adapter connecting the tubular member to the waste collection bag.

In FIGS. 3 and 4, the control device 10 includes a tubular body member 14 having inner and outer ends 16 and 18 on opposite sides of a stoma opening 19.

A balloon valve 20 is attached to the interior sidewall 22 of the tubular member 14 and is inflated and deflated through a passageway 24 in the tubular member sidewall. An annular recess 26 is formed in the sidewall of the tubular member 14 to matingly engage the inflated balloon 20 along its circumferencial perimeter and thus provide a sealing seat which prevents the flow of waste materials through the passageway 24 when the balloon 20 is inflated.

An umbrella 28 is attached to the inner end 16 of the tubular member 14 and is engaged by a doughnut-shaped balloon 30 embracing the inner end 16 of the tubular member 14 and pressing downwardly on the inner end of the radially extending umbrella 28 which extends forwardly and outwardly when in an opened condition as seen in FIGS. 3 and 4. The umbrella 28 includes a memory which causes it to return to a closed position coaxial with the tubular member 14 when the balloon 30 is deflated. A passageway 32 in the sidewall of the tubular member 14 connects with the balloon 30. The pressure generated by the balloon 30 applied to the umbrella may of course vary as required to form a seal at the interface 34 between the umbrella and the interior wall 36 surrounding the stoma opening 19.

A bag adapter end piece 38 is provided on the outer end 18 of the tubular member 14. The adapter 38 includes a tube portion 40 adapted to be telescopically received in the outer free end 18 of the tubular member 14. Axially forwardly extending conduit tubes 42 and 44 are received in the conduits 32 and 24 respectively. Laterally outwardly extending tube portions 46 and 48 are engagable by a hypodermic needle or a cannula and the tube portions 46 and 48 include self sealing micro valves 49 for inflating and deflating the balloons.

The bag adapter 38 includes an outwardly facing enlarged mouth 50 having an annular shoulder 52 adapted to be received in an annular groove 54 on a complimentarily shaped mouth 56 carried on a bag 58.

Figure 5:
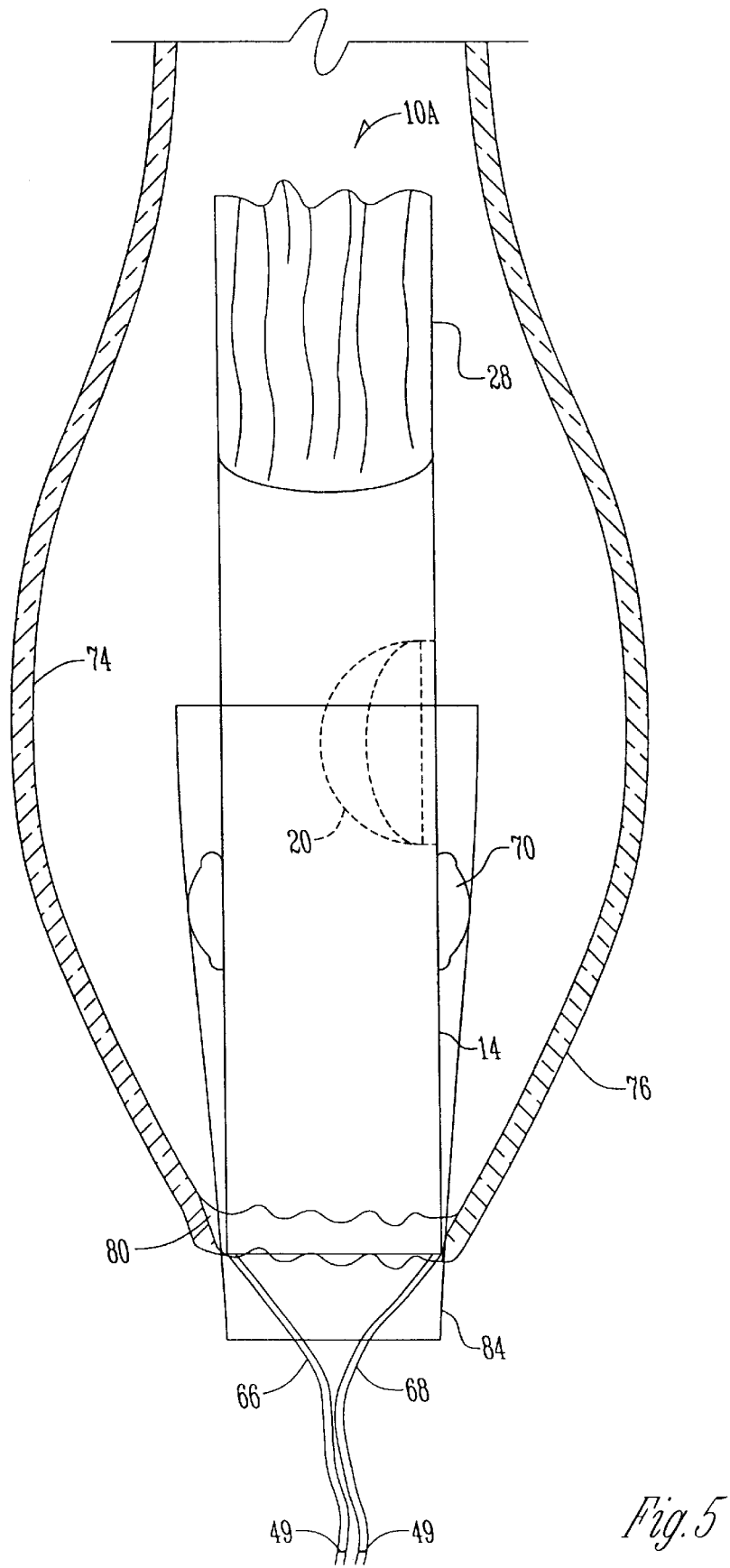
FIG. 5 is a cross-sectional view of an alternative embodiment of the control device being positioned in the rectum.
Figure 6:
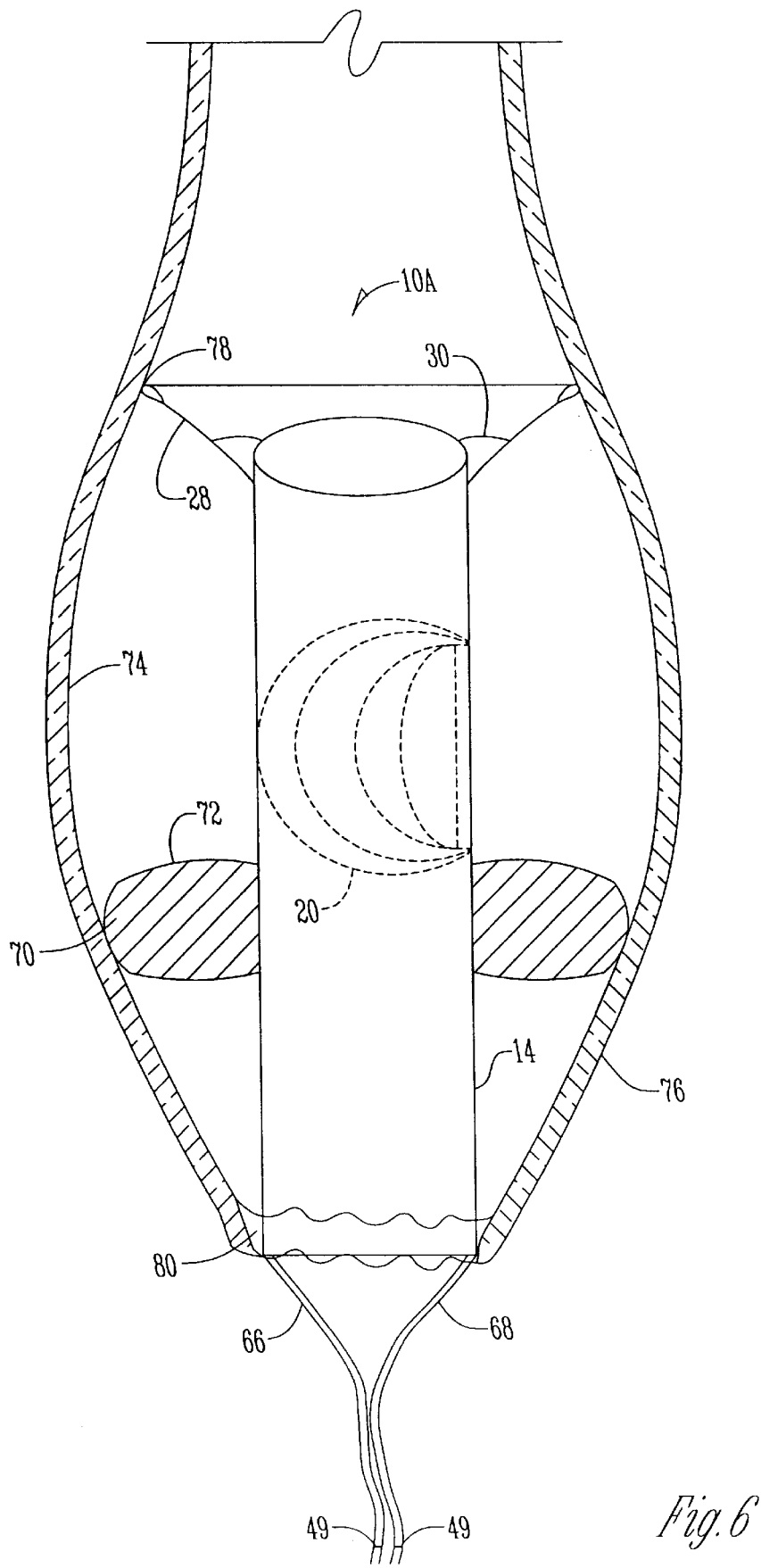
FIG. 6 is a view similar to FIG. 5 but showing the control device with the umbrella having been expanded by the umbrella balloon being inflated.

An alternative feces control device is shown in FIGS. 5 and 6 and is referred to generally by the Reference 10A and is similar to the control device 10 except that an adapter 38 is not used since the control device 10A is positioned in the rectum allowing conventional discharge of waste upon operation of the balloon valve 20. The umbrella balloon 30 and the balloon valve 20 have their inflation conduits 32 and 24 respectively connected to flexible inflation tubes 66 and 68 respectively which extend to the outside of the body for accessing an inflation device such as the hypodermic needle or cannula and for providing a handle for removing the control device 10A when desired.

A doughnut-shaped retainer 70 is slidably mounted on the tubular member 14 with the outer peripheral surface 72 of the retainer 70 engaging the sidewall 74 of the rectum 76. The soft tissue of the sidewall tends to absorb the outer edge 72 of the retainer 70 and thus anchor it in position limiting further travel inwardly or outwardly within the rectum and thus functioning to maintain a seal at the interface 78 between outer peripheral edge of the umbrella 28 and the sidewall 74 of the rectum 76. It is further seen that the anal sphincter 80 embracing the tubular member 14 further assists in anchoring the control device 10A against longitudinal movement in or out of the rectum 76.

In FIG. 5, an inserter sleeve 84 is utilized for inserting the control device 10A into the rectum 76. Once the control device 10A has been inserted, the inserter sleeve 84 is removed and the balloon valve 20 and umbrella balloon 30 are inflated. Removal of the control device 10A is accomplished by pulling on the inflation tubes 66 and 68 after the umbrella balloon 30 has been deflated and the umbrella has returned in response to its inherent memory to the position of FIG. 5 coaxial with the tubular member 14.

What is claimed is:

1. A feces control device comprising,
    a tubular member having inner and outer ends interconnected by a passageway, said tubular member having a sidewall with inner and outer faces, said passageway being defined by said inner sidewall face, and
    an inflatable balloon valve positioned in said passageway for selectively allowing passage of fecal material therethrough.

2. The feces control device of claim 1 wherein said balloon valve is secured to said sidewall on one side thereof and upon inflation expands across said passageway into sealing engagement with the entire inner circumference of the sidewall inner face in the transverse plane of said balloon valve.

3. The feces control device of claim 2 wherein said sidewall includes an inflation conduit extending from said balloon valve to the outer end of said tubular member for engagement by an inflation device for inflating and deflating said balloon.

4. The feces control device of claim 1 wherein said tubular member includes an umbrella shaped member on the inner end thereof operational between a collapsed closed shape coaxial with said tubular member and an expanded open shape.

5. The feces control device of claim 4 wherein said umbrella includes inner and outer ends with said outer end being free and said inner end engaging the inner end of said tubular member along its entire circumferencial perimeter.

6. The feces control device of claim 5 and an umbrella balloon is positioned on the inner end of said umbrella around the inner end of said tubular member for operation between inflated and deflated conditions, said umbrella balloon when inflated pressing against the inner end of said umbrella member for moving said umbrella to said expanded open shape.

7. The feces control device of claim 6 wherein said umbrella balloon is positioned on said umbrella inner end opposite said tubular member.

8. The feces control device of claim 7 wherein said umbrella when in its expanded open shape extends radially outwardly and forwardly from the inner end of said tubular member.

9. The feces control device of claim 8 wherein said tubular member sidewall includes an inflation conduit extending between said umbrella balloon and said outer end of said tubular member.

10. The feces control device of claim 9 and a bag adapter end piece is positioned on the outer end of said tubular member engaging one side of said bag adapter end piece with the opposite side being engaged by a bag.

11. The feces control device of claim 10 wherein said bag adapter end piece includes an inflation conduit portion engaging said tubular member conduit.

12. The feces control device of claim 11 wherein said conduit portion is telescopically received in said tubular member conduit.

13. The feces control device of claim 1 and a retainer is provided on said tubular member for being selectively positioned longitudinally thereof for engagement with the rectum sidewall.

14. A feces control device comprising,
    a tubular member having inner and outer ends interconnected by a passageway, said tubular member having a sidewall with inner and outer faces, said passageway being defined by said inner sidewall face, and
    said tubular member including an umbrella shaped member on the inner end thereof operational between a collapsed closed shape coaxial with said tubular member and an expanded open shape.

15. The feces control device of claim 14 wherein said umbrella includes inner and outer ends with said outer end being free and said inner end engaging the inner end of said tubular member along its entire circumferencial perimeter.

16. The feces control device of claim 15 and an umbrella balloon is positioned on the inner end of said umbrella around the inner end of said tubular member for operation between inflated and deflated conditions, said umbrella balloon when inflated pressing against the inner end of said umbrella holder for moving said umbrella to said expanded open shape.

17. The feces control device of claim 16 wherein said umbrella balloon is positioned on said umbrella inner end opposite said tubular member.

18. The feces control device of claim 17 wherein said umbrella when in its expanded open shape extends radially outwardly and forwardly from the inner end of said tubular member.

19. The feces control device of claim 18 wherein said tubular member sidewall includes an inflation conduit extending between said umbrella balloon and said outer end of said tubular member.

20. A feces control device comprising,
    a tubular member having inner and outer ends interconnected by a passageway, said tubular member having a sidewall with inner and outer faces, said passageway being defined by said inner sidewall face,
    an inflatable balloon valve positioned in said passageway for selectively allowing passage of fecal material therethrough, and
    said tubular member including an umbrella shaped member on the inner end thereof operational between a collapsed closed shape coaxial with said tubular member and an expanded open shape.

21. The feces control device of claim 18 and an inflation conduit extends between said balloon valve and said outer end of said tubular member, and inflation tube end pieces are connected to said balloon valve conduit and to said umbrella balloon conduit for connection to inflation means and for removal of said device from the rectum.

22. A material flow control device comprising,
    a tubular member having inner and outer ends interconnected by a passageway, said tubular member having a sidewall with inner and outer faces, said passageway being defined by said inner sidewall face, and
    an inflatable balloon valve positioned in said passageway for selectively allowing passage of material therethrough.

23. The material flow control device of claim 22 wherein said balloon valve is secured to said sidewall on one side thereof and upon inflation expands across said passageway into sealing engagement with the entire inner circumference of the sidewall inner face in the transverse plane of said balloon valve.

24. The material flow control device of claim 23 wherein said sidewall includes an inflation conduit extending from said balloon valve to the outer end of said tubular member for engagement by an inflation device for inflating and deflating said balloon.

25. The material flow control device of claim 22 wherein said tubular member includes an umbrella shaped member on the inner end thereof operational between a collapsed closed shape coaxial with said tubular member and an expanded open shape.

26. The material flow control device of claim 25 wherein said umbrella includes inner and outer ends with said outer end being free and said inner end engaging the inner end of said tubular member along its entire circumferencial perimeter.

27. The material flow control device of claim 26 and an umbrella balloon is positioned on the inner end of said umbrella around the inner end of said tubular member for operation between inflated and deflated conditions, said umbrella balloon when inflated pressing against the inner end of said umbrella member for moving said umbrella to said expanded open shape.

28. The material flow control device of claim 27 wherein said umbrella balloon is positioned on said umbrella inner end opposite said tubular member.

29. The material flow control device of claim 28 wherein said umbrella when in its expanded open shape extends radially outwardly and forwardly from the inner end of said tubular member.

30. The material flow control device of claim 29 wherein said tubular member sidewall includes an inflation conduit extending between said umbrella balloon and said outer end of said tubular member.

31. The material flow control device of claim 30 and a bag adapter end piece is positioned on the outer end of said tubular member engaging one side of said bag adapter end piece with the opposite side being engaged by a bag.

32. The material flow control device of claim 31 wherein said bag adapter end piece includes an inflation conduit portion engaging said tubular member conduit.

33. The material flow control device of claim 32 wherein said conduit portion is telescopically received in said tubular member conduit.

34. The material flow control device of claim 22 and a retainer is provided on said tubular member for being selectively positioned longitudinally thereof for engagement with a body opening sidewall.

35. A material flow control device comprising, a tubular member having inner and outer ends interconnected by a passageway, said tubular member having a sidewall with inner and outer faces, said passageway being defined by said inner sidewall face, and said tubular member including an umbrella shaped member on the inner end thereof operational between a collapsed closed shape coaxial with said tubular member and an expanded open shape.

36. The material flow control device of claim 35 wherein said umbrella includes inner and outer ends with said outer end being free and said inner end engaging the inner end of said tubular member along its entire circumferencial perimeter.

37. The material flow control device of claim 36 and an umbrella balloon is positioned on the inner end of said umbrella around the inner end of said tubular member for operation between inflated and deflated conditions, said umbrella balloon when inflated pressing against the inner end of said umbrella holder for moving said umbrella to said expanded open shape.

38. The material flow control device of claim 37 wherein said umbrella balloon is positioned on said umbrella inner end opposite said tubular member.

39. The material flow control device of claim 38 wherein said umbrella when in its expanded open shape extends radially outwardly and forwardly from the inner end of said tubular member.

40. The material flow control device of claim 39 wherein said tubular member sidewall includes an inflation conduit extending between said umbrella balloon and said outer end of said tubular member.

41. A material flow control device comprising, a tubular member having inner and outer ends interconnected by a passageway, said tubular member having a sidewall with inner and outer faces, said passageway being defined by said inner sidewall face, an inflatable balloon valve positioned in said passageway for selectively allowing passage of material therethrough, and said tubular member including an umbrella shaped member on the inner end thereof operational between a collapsed closed shape coaxial with said tubular member and an expanded open shape.

42. The material flow control device of claim 39 and an inflation conduit extends between said balloon valve and said outer end of said tubular member, and inflation tube end pieces are connected to said balloon valve conduit and to said umbrella balloon conduit for connection to inflation means and for removal of said device from the body.

* * * * *